United States Patent [19]

Hooper et al.

[11] 4,134,838

[45] Jan. 16, 1979

[54] FABRIC CONDITIONING PRODUCT

[75] Inventors: David C. Hooper, Ashford; George A. Johnson; Donald Peter, both of Wirral, all of England

[73] Assignee: Lever Brothers Company, New York, N.Y.

[21] Appl. No.: 878,133

[22] Filed: Feb. 15, 1978

[30] Foreign Application Priority Data

Feb. 15, 1977 [GB] United Kingdom ................ 6249/77

[51] Int. Cl.$^2$ ............................................ D06M 13/34
[52] U.S. Cl. .................................... 252/8.8; 252/8.6; 252/522; 424/65
[58] Field of Search ...................... 252/8.6, 8.8, 522; 424/65

[56] References Cited

U.S. PATENT DOCUMENTS

| 3,101,297 | 8/1963 | Hack ..................................... 252/8.6 |
| 3,271,305 | 9/1966 | Allen et al. ........................... 252/8.6 |
| 3,637,495 | 1/1972 | Eckert et al. ......................... 252/8.6 |
| 3,644,204 | 2/1972 | Heins et al. .......................... 252/8.6 |
| 3,790,484 | 2/1974 | Blair .................................... 252/8.6 |
| 3,943,242 | 3/1976 | Fogel et al. ........................... 424/65 |

*Primary Examiner*—William E. Schulz
*Attorney, Agent, or Firm*—Melvin H. Kurtz

[57] ABSTRACT

A fabric conditioning composition comprises a fabric softening amount of a fabric softener and a deodorizing amount of a deodorant perfume, the composition having an odor reduction value within the range of from 0.50 to 3.5 as measured by the modified Whitehouse and Carter test.

12 Claims, No Drawings

FABRIC CONDITIONING PRODUCT

This invention relates to fabric conditioning compositions which are capable of softening and deodorising fabric, and to processes for preparing such compositions. More particularly, the invention is concerned with compositions which additionally impart to the fabric of a garment the property of suppressing body malodour when the garment is subsequently worn adjacent the skin.

BACKGROUND TO THE INVENTION

It has long been recognised that the development of body malodour is at least partly due to bacterial action on the products of the sweat glands. Washing with a detergent, for example in the form of a personal washing bar such as a soap bar, removes malodorous products and reduces the concentration of bacteria on the skin. Complete elimination of bacteria cannot usually be achieved by this means, and in any case it is not usually convenient to wash the skin, particularly the axillae where body malodour development is most likely to originate, repeatedly or at regular intervals during the day when physical exercise which induces sweating is likely to lead to conditions which suit the accumulation of body malodour materials.

It would therefore be advantageous to provide continuous protection against the development of body malodour when washing was not feasible or convenient.

Personal deodorant products in the form of aerosol sprays, roll-ball and sticks, are available to combat this problem, but as with personal washing, such products must be applied to the skin, particularly the axillae at regular intervals if the development of body malodour is to be prevented. Many of the commercially available personal products of this type are however of limited effectiveness or suffer from certain drawbacks. As an example, when such products contain a germicide as the deodorant active material for reducing the bacterial load on the skin which would otherwise give rise to body malodour, staining of clothing adjacent the treated skin can occur.

It would therefore be advantageous if prolonged protection against the development of body malodour could be provided without the need to wash repeatedly or apply a personal deodorant product to the skin at frequent intervals.

It has now been discovered that protection against the development of body malodour can be achieved by treating garments intended to be worn in contact with the skin with a special perfume which is described herein as a deodorant perfume.

SUMMARY OF THE INVENTION

Perfumes have been used as odour maskants since ancient times, particularly when applied directly to the skin, but the perfuming of garments intended to be worn adjacent the skin has not hitherto succeeded in effectively masking body malodour. This is at least partly due to the problem of reliably delivering perfume to the fabric of such garments in a manner to make them effective over a long period of time in eliminating detectable body malodour components, and also to the inherent inability of perfumes to successfully mask the more potent odourous compounds which contribute to body malodour.

It has now been discovered that certain combinations of perfume materials, hereinafter referred to as deodorant perfumes, when incorporated in the fabric of a garment together with a fabric softening material are capable of imparting to the fabric of that garment the property of reducing body malodour when the garment is subsequently worn in contact with the skin.

The effectiveness of deodorant perfumes when employed in this way can be measured by a test based on that devised by Whitehouse & Carter as published in The Proceedings of the Scientific Section of the Toilet Goods Association, Number 48, December 1967, at pages 31 to 37, under the title "Evaluation of Deodorant Toilet Bars."

The test described in that publication was modified in four ways: firstly, the product to be evaluated was the deodorant fabric conditioning composition of the invention which was applied, as described hereinafter, to a fabric during the wash, rinse or drying cycle of a laundry process, instead of a soap bar used to wash the axillae of human subjects, secondly, a 0 to 5 instead of a 0 to 10 grading scale was employed as a basis for determining the odour reduction value, thirdly, grading of odour intensity was performed 5 hours after treatment instead of 24 hours, and fourthly, the odour of that part of a treated shirt which had been worn in contact with the axillae was assessed rather than the axillae themselves of the wearer.

In carrying out the test, the fabric conditioning composition should be applied to fabric in a standard manner. The procedure to be adopted for each of two different types of composition — a liquid composition and an impregnated substrate — is outlined below. It is to be understood that similar standard procedures for application of liquid, solid or impregnated substrate fabric conditioning compositions to fabric via the wash, rinse or drying cycle, other than those standard procedures described below, can be devised.

Application of a liquid fabric conditioning composition to fabric from the rinse cycle of a laundry process Polyester cotton coat style button through shirts were first prewashed in an automatic washing machine using a nonionic detergent fabric washing powder. This was to ensure that the shirts to be used in the test were all equally clean and free from dressing prior to application of the fabric conditioning composition.

The washed shirts were line dried and then washed again in the automatic washing machine. The test liquid fabric conditioning composition containing di-(hardened tallow) dimethylammonium chloride as a fabric softener at a concentration of 6% by weight of the composition and a deodorant perfume at a concentration of 0.2% by weight of the composition was then added to the rinse liquor at a concentration of 0.2% by weight of the liquor. The ratio of shirt fabric (dry weight basis) to rinse liquor was 40g fabric per liter rinse liquor.

The shirts were agitated in the rinse liquor for 5 minutes at a temperature of from 15° to 20° C., then spun to a moisture content of about 50% water and finally line dried to a moisture content of not greater than 10%.

A further batch of prewashed shirts which were to serve as control shirts were rinsed and then dried under similar conditions except that deodorant perfume was omitted from the fabric conditioning composition added to the rinse liquor.

The shirts were folded and stored overnight in polyethylene bags until required for testing by a panel of male subjects and assessing for odour by a panel of female assessors.

The above procedure was repeated on four consecutive days without prewashing the shirts, half of the subjects wearing shirts treated with the deodorant perfume containing fabric conditioner and half wearing control shirts without deodorant perfume treatment.

Application of a fabric conditioning composition to fabric from an impregnated substrate in a tumble drier Polyester cotton coat style button through shirts were prewashed, rinsed and dried as described above and then wetted out to a moisture content of 75%.

Tissues to serve as the substrate for impregnation with a fabric conditioning composition were made from non-woven textile fibres comprising a polyester substrate and weighing 32–34 g/m$^2$ and having a water absorption capacity of 3.3. The tissues were impregnated with the fabric conditioning composition consisting of 3 parts by weight of di-(hardened tallow) dimethylammonium chloride as a fabric softener and 1 part by weight of the condensation product of a secondary linear $C_{11-15}$ alcohol 12EO as a nonionic dispersant and deodorant perfume at a concentration of 2% by weight of the composition to provide an add-on of the fabric conditioning composition of 0.66g per 100 cm$^2$ tissue: the impregnation temperature employed was about 50° C.

A 1400g load (dry weight basis) of the unbuttoned wetted out shirts was tumble dried in the presence of a tissue (28 cm × 23 cm), impregnated with the test fabric conditioning composition, for 45 minutes at an exit air temperature ranging from 25° C. at the start to 77° C. at the finish.

A further batch of prewashed shirts which were to serve as control shirts were tumble dried under similar conditions except that deodorant perfume was omitted from the fabric conditioning composition with which the tissue was impregnated.

The shirts were folded and stored until required for testing as described hereinbefore.

The above procedure was repeated on four consecutive days without prewashing the shirts, half of the subjects wearing shirts treated with deodorant perfume containing fabric conditioner and half wearing control shirts without deodorant perfume treatment.

It is to be understood that the invention is not limited to the use of the quaternary ammonium fabric softener employed in the above described tests. Other fabric softeners, as hereinafter defined, will give comparable odour reduction values within the scope of the invention when the effectiveness of the fabric conditioning compositions of the invention is assessed according to the appropriate test method.

Odour reduction value

For a treated shirt to be effective in reducing body malodour, it is necessary for the odour reduction value of the shirt to be at least 0.50.

Preferably, the odour reduction value is at least 0.70, more preferably at least 1.00 and most preferably at least 1.20. It is clear that the deodorant effect demonstrated in this way is not solely that of odour masking, since in many instances there is no detectable smell of perfume on the treated fabric after a few hours. Accordingly, the use of deodorant perfumes in the manner described represents a new operative principle.

In the course of attempting to characterise this new principle, many hundreds of known perfume materials have been screened. Hundreds of formulations made by blending materials have been examined, including a number of commercial perfumes whose formulations are not fully known (being confidential to the perfumery house in question offering the perfume for sale). No commercial perfume has been found that is capable of giving a treated fabric the malodour inhibiting property attributable to a deodorant perfume. This supports the view that a new principle of an entirely unexpected kind has been discovered.

Definition of the Invention

In its widest aspect, the invention provides a fabric conditioning composition comprising an effective amount of a fabric softener and a deodorising amount of a deodorant perfume, the fabric conditioning composition having an odour reduction value within the range of from 0.50 to 3.5 as measured by the modified Whitehouse and Carter test.

The invention also provides a process for preparing a fabric conditioning composition which process comprises mixing a deodorant perfume, and a fabric softener to provide a fabric conditioning composition having an odour reduction value within the range of from 0.50 to 3.5 as measured by the modified Whitehouse and Carter test.

The invention furthermore provides a method for suppressing human body malodour which comprises contacting the skin with a fabric treated with a fabric conditioning composition said composition comprising a deodorant perfume and a fabric softener, the composition having an odour reduction value within the range of from 0.50 to 3.5 as measured by the modified Whitehouse and Carter test.

Fabric Softeners

The fabric conditioning composition according to the present invention comprises compounds generally classified as fabric softeners that are employed during the washing, rinsing or drying cycle of the home laundering operation. Such fabric softeners are inorganic clays or water-soluble or water-dispersible organic, waxy materials having a preferred melting (or softening) point between about 25° C. and 150° C. Softener materials of this type are also fabric substantive in the sense that they are readily deposited onto the surfaces of fabrics treated therewith. Many fabric softeners of this type also impart some degree of static control to the fabrics being treated therewith.

The fabric softeners can be used singly or, in admixture with one or more compatible fabric softeners. They can be selected from the following broadly denoted classes of compounds which contain at least one long chain group:

(1) cationic quaternary ammonium salts including quaternary imidazolinium salts
(2) nonionic compounds, such as sorbitan esters, tertiary amine oxides and ethyoxylated alcohols and alkylphenols;
(3) anionic soaps, sulfates and sulfonates, e.g. fatty acid soaps, ethoxylated alcohol sulfates and sodium alkyl sulfates, alkyl sulfonates, sodium alkylbenzene sulfonates, and sodium or potassium alkylglycerylethersulfonates;

(4) Zwitterionic quaternary ammonium compounds;
(5) ampholytic tertiary ammonium compounds; and
(6) smectite-type inorganic clays.

Particularly preferred softening agents are the cationic quaternary ammonium salts which have the general formula

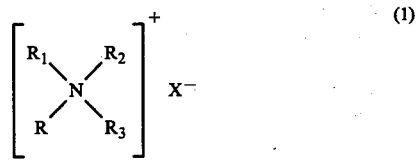

where X is an anion, preferably a halide and more particularly, a chloride ion. Other suitable anions can include acetate, phosphate, nitrate and methyl sulfate radicals. Additionally, in the above formula, R and $R_1$ represent benzyl or an alkyl containing from 1 to 3 carbon atoms, or an alkyl of from 12 to 20 carbon atoms, or alkoxypropyl or hydroxy substituted alkoxypropyl radicals, where the alkoxy contains 12 to 20 carbon atoms, and $R_2$ represents an alkyl containing from 12 to 20 carbon atoms. The carbon chains of $R_3$ and $R_2$, whenever $R_2$ represents a chain of from 12 to 20 carbon atoms, can be straight or branched, and saturated or unsaturated.

The most preferred cationic softening agents are dialkyl dimethyl ammonium chloride or alkyl trimethyl ammonium chloride where the alkyl contains from 12 to 20 carbon atoms and are derived from long chain fatty acids, especially from hydrogenated tallow. The terms "tallow" and "tallowalkyl" are intended to mean alkyls containing from 16 to 18 carbon atoms. The term "tallowalkoxy" means an alkyl ether radical wherein the alkyl contains from 16 to 18 carbon atoms. Specific examples of the particularly preferred cationic softening agents include the following:

tallowtrimethyl ammonium chloride
tallowdimethyl (3-tallowalkoxypropyl) ammonium chloride
ditallow dimethyl ammonium chloride
ditallow dimethyl ammonium methyl sulfate
eicosyltrimethyl ammonium chloride, and
dieicosyldimethyl ammonium chloride.

Examples of other preferred cationic softening agents suitable for use in the invention herein include the following:

dodecyltrimethyl ammonium chloride
didodecyldimethyl ammonium chloride
tetradecyltrimethyl ammonium chloride
ditetradecyldimethyl ammonium chloride
pentadecyltrimethyl ammonium chloride
dipentadecyldimethyl ammonium chloride
didodecyldiethyl ammonium chloride
didodecyldipropyl ammonium chloride
ditetradecyldiethyl ammonium chloride
ditetradecyldipropyl ammonium chloride
ditallowdiethyl ammonium chloride
ditallowdipropyl ammonium chloride
tallowdimethyl benzyl ammonium chloride
tallowdiethyl benzyl ammonium chloride
dodecyltrimethyl ammonium methyl sulfate
didodecyldiethyl ammonium acetate
tallowtrimethyl ammonium acetate
tallowdimethyl benzyl ammonium nitrite and
ditallowdipropyl ammonium phosphate Other cationic softening agents of Formula 1 include the variation where R and $R_1$ can also represent a phenyl radical or a hydroxy substituted alkyl of from 1 to 3 carbon atoms.

Cationic quaternary imidazolinium compounds are also preferred as softening agents. These compounds conform to the formula:

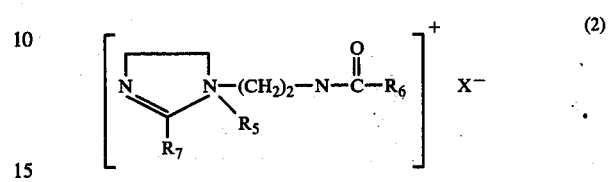

wherein $R_5$ is an alkyl containing from 1 to 4, preferably from 1 to 2, carbon atoms, $R_6$ is an alkyl containing from 1 to 4 carbon atoms or a hydrogen radical, $R_7$ is an alkyl containing from 8 to 25, preferably at least 15 carbon atoms, $R_4$ is hydrogen or an alkyl containing from 8 to 25, preferably at least 15, carbon atoms, and X is an anion, preferably methyl sulfate or chloride ions. Other suitable anions include those disclosed with reference to the cationic softening agents of Formula 1. Particularly preferred are those compounds of Formula 2 in which both $R_4$ and $R_7$ are alkyls of from 16 to 25, especially 16 to 18 and 20 to 22, carbon atoms.

Many other cationic quaternary ammonium softening agents are known; for example, alkyl ($C_{12}$ to $C_{20}$) - pyridinium chlorides, alkyl ($C_{12}$ to $C_{20}$) — alkyl ($C_1$ to $C_3$) — morpholinium chlorides, and quaternary derivatives of amino acids and amino esters.

The fabric softeners can also comprise certain cationic alkylated and acylated diamine materials and their acid salts. Useful diamine fabric softeners have the general formula:

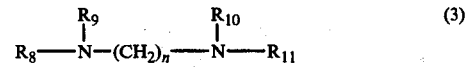

where $R_8$ is an alkyl or acyl group containing from about 12 to 20 carbon atoms; $R_9$ and $R_{10}$ are hydrogen or alkyl of form about 1 to 20 carbon atoms and $R_{11}$ is hydrogen, $C_{1-20}$ alkyl or $C_{12-20}$ acyl. At least two of $R_9$, $R_{10}$ and $R_{11}$ are hydrogen or alkyl containing 1 to 3 carbon atoms, and n is from 2 to 5.

Examples of such alkylated diamine compounds include:

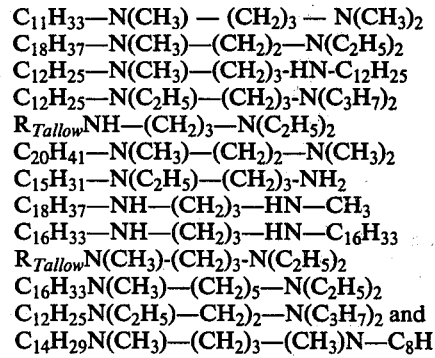

where in the above formulas $R_{Tallow}$ is the alkyl group derived from tallow fatty acid.

Other examples of suitable alkylated diamine compounds include N-tetradecyl, N'-propyl-1,3-propanediamine; N-eicosyl, N,N',N'-triethyl-1,2-ethane-diamine and N-octadecyl, N,N',N'-tripropyl-1,3-propane-diamine.

Examples of suitable acylated diamine fabric softeners include $C_{13-20}$ amido amine derivatives.

Acid salts of the above-described diamine compounds can also be employed as fabric softeners. Such materials include those derived from hydrochloric acid, acetic acid, sulfuric acid, sulfonic acid, formic acid and citric acid.

Other preferred softening agents include Zwitterionic quaternary ammonium compounds which have the formula

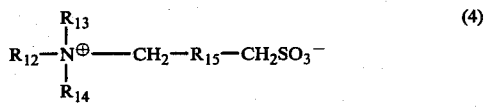

where $R_{13}$ and $R_{14}$ are each methyl, ethyl, n-propyl, isopropyl, 2-hydroxyethyl or 2-hydroxypropyl, $R_{12}$ is a 20 to 30 carbon atom alkyl or alkenyl and where said alkyl or alkenyl contains from 0 to 2 hydroxyl substituents, from 0 to 5 ether linkages, and from 0 to 1 amide linkage, and $R_{15}$ is an alkylene group containing from 1 to 4 carbon atoms with from 0 to 1 hydroxyl substituents; particularly preferred are compounds where $R_{12}$ is a carbon chain containing from 20 to 26 carbon atoms selected from alkyls and alkenyls and where said alkyls and alkenyls contain 0 to 2 hydroxyl substituents. Specific examples of the particularly preferred compounds of this class include the following:

3-N-eicosyl-N,N-dimethylammonio)-2-hydroxypropane-1-sulfonate
3-(N-eicosyl-N,N-dimethylammonio)-propane-1-sulfonate
3-[N-eicosyl-N,N-di(2-hydroxyethyl)ammonio]-2-hydroxypropanesulfonate
3-(N-docosyl-N,N-dimethylammonio)-2-hydroxypropane-1-sulfonate
3-(N-docosyl-N,N-dimethylammonio)-propane-1-sulfonate
3-[N-docosyl-N,N-bis-(2-hydroxyethyl)ammonio]-2-hydroxypropane-1-sulfonate
3-(N-tetracosyl-N,N-dimethylammonio)-2-hydroxypropane-1-sulfonate
3-(N-tetracosyl-N,N-dimethylammonio)-propane-1-sulfonate
3-[N-tetracosyl-N,N-bis-(2-hydroxyethyl)ammonio]-2-hydroxypropane-1-sulfonate
3-(N-hexacosyl-N,N-dimethylammonio)-2-hydroxypropane-1-sulfonate
3-(N-hexacosyl-N,N-dimethylammonio)-propane-1-sulfonate Examples of other preferred compounds of this class are as follows:

3-(N-eicosyl-N-ethyl-N-methylammonio)-2-hydroxypropane-1-sulfonate
3-(N-docosyl-N-ethyl-N-methylammonio)-2-hydroxypropane-1-sulfonate
3-(N-tetracosyl-N-ethyl-N-methylammonio)-2-hydroxypropane-1-sulfonate
3-(N-heneicosyl-N,N-dimethylammonio)-2-hydroxypropane-1-sulfonate
3-(N-tricosyl-N,N-dimethylammonio)-2-hydroxypropane-1-sulfonate
3-(N-tricosyl-N-ethyl-N-methylammonio)-2-hydroxypropane-1-sulfonate
3-(N-tricosyl-N,N-dimethylammonio)-propane-1-sulfonate
3-(N-pentacosyl-N,N-dimethylammonio-2-hydroxypropane-1-sulfonate
3-[N-(2-methoxydocosyl)-N,N-dimethylammonio]-2-hydroxypropane-1-sulfonate
3-(N-heptacosyl-N,N-dimethylammonio)-propane-1-sulfonate
3-(N-octacosyl-N,N-dimethylammonio)-2-hydroxypropane-1-sulfonate
3-(N-monacosyl-N,N-dimethylammonio)-2-hydroxypropane-1-sulfonate
3-(N-triacontyl-N,N-dimethylammonio)-propane-1-sulfonate
3-[N-(3,5-dioxatetracosyl)-N,N-dimethylammonio]-2-hydroxy propane-1-sulfonate Other Zwitterionic compounds useful as softening agents include Zwitterionic synthetic detergents as represented by derivatives of aliphatic quaternary ammonium compounds where one of the four aliphatic groups has about 8 to 20 carbon atoms, another contains a water-solubilizing group (e.g., carboxy, sulfato or sulfo groups), and any of which are straight or branched.

Nonionic tertiary phosphine oxide compounds are also preferred softening agents. These compounds have the generic formula

where $R_{16}$ is alkyl, alkenyl, or monohydroxy alkyl having a chain length of from 20 to 30 carbon atoms, and where $R_{17}$ and $R_{18}$ are each methyl, ethyl or ethanol. Specific examples of particularly preferred softeners of this class include the following:

eicosyldimethylphosphine oxide,
eicosyldi(2-hydroxyethyl)phosphine oxide,
docosyldimethylphosphine oxide,
docosyldi(2-hydroxyethyl)phosphine oxide,
tetracosyldimethylphosphine oxide,
hexacosyldimethylphosphine oxide,
eicosyldiethylphosphine oxide,
docosyldiethylphosphine oxide, and
tetracosyldi(2-hydroxyethyl)phosphine oxide.

Examples of other preferred tertiary phosphine oxides of this class are as follows:

eicosylmethylethylphosphine oxide,
heneicosyldimethylphosphine oxide,
β-hydroxyeicosyldimethylphosphine oxide,
β-hydroxydocosyldimethylphosphine oxide,
heneicosylmethylethylphosphine oxide,
docosylmethylethylphosphine oxide,
tricosyldiethylphosphine oxide,
tricosyldimethylphosphine oxide,
tetracosyldi(2-hydroxyethyl)phosphine oxide,
pentacosyldimethylphosphine oxide,
eicosylmethyl-2-hydroxybutylphosphine oxide,
eicosyldibutylphosphine oxide,
docosylmethyl-3-hydroxybutylphosphine oxide,
hexacosyldiethylphosphine oxide,
heptacosyldimethylphosphine oxide,
octacosyldiethylphosphine oxide,
triacontyldimethylphosphine oxide.

Other nonionic tertiary phosphine oxides include the nonionic synthetic detergents having the same formula as that of Formula 5 above where $R_{16}$ is an alkyl, alkenyl, or monohydroxyalkyl of from 10 to 20 carbon atoms, and where $R_{17}$ and $R_{18}$ are each alkyl or monohydroxyalkyl of from 1 to 3 carbon atoms.

Nonionic tertiary amines oxides are also known to be useful as softening agents and can be utilized in the compositions of the present invention. These nonionic compounds have the formula $$R_{19}R_{20}R_{21}N \rightarrow O \qquad (6)$$

where $R_{19}$ represents a straight or branched chain alkyl of alkenyl containing from 20 to 30 carbon atoms and from 0 to 2 hydroxyl substituents, from 0 to 5 ether linkages, there being at least one moiety of at least 20 carbon atoms containing no ether linkages, and 0 to 1 amide linkage, and where $R_{20}$ and $R_{21}$ are each alkyl or monohydroxy alkyl containing from 1 to 4 carbon atoms and where $R_{20}$ and $R_{21}$ can be joined to form a heterocyclic group containing from 4 to 6 carbon atoms; particularly preferred are those wherein $R_{19}$ is a straight or branched alkyl, alkenyl, or monohydroxy alkyl containing 20 to 26 carbon atoms and where $R_{20}$ and $R_{21}$ are each methyl, ethyl or ethanol.

Specific examples of the particularly preferred compounds of this class are as follows:
eicosyl-bis-($\beta$-hydroxyethyl) amine oxide,
eicosyldimethylamine oxide,
docosyldimethylamine oxide,
docosyl-bis-($\beta$-hydroxyethyl) amine oxide,
tetracosyldimethylamine oxide,
tetracosyl-bis-($\beta$-hydroxyethyl) amine oxide,
hexacosyldimethylamine oxide, and
hexacosyl-bis-($\beta$-hydroxyethyl) amine oxide.

Examples of other preferred tertiary amine oxides of this class are as follows:
2-hydroxyeicosyldimethylamine oxide,
eicosylmethylethylamine oxide,
eicosyldiethylamine oxide,
2-hydroxyeicosyldiethylamine oxide,
heneicosyldimethylamine oxide,
heneicosyldiethylamine oxide,
docosyldiethylamine oxide,
tricosyldimethylamine oxide,
tricosylidiethylamine oxide,
tetracosyldiethylamine oxide,
$\beta$-hydroxytetracosyldimethylamine oxide,
pentacosyldimethylamine oxide,
hexacosyldiethylamine oxide,
eicosylmethyl(2-hydroxypropyl) amine oxide,
docosylbutylmethylamine oxide,
2-docosenyldimethylamine oxide,
2-methoxydocosyldimethylamine oxide,
heptacosyldimethylamine oxide,
octacosylmethylethylamine oxide,
octacosyldiethylamine oxide,
nonacosyldimethylamine oxide,
triacontyldiethylamine oxide,
3,6-dioxaoctascosyldimethylamine oxide,
2-hydroxy-4-oxatetracosyldimethylamine oxide,
6-stearamidohexyldimethylamine oxide.

Other tertiary amine oxides include compounds corresponding to Formula 6 above where $R_{19}$ is an alkyl of 8 to 20, particularly 16 to 18, carbon atoms, and $R_{20}$ and $R_{21}$ are methyl or ethyl radicals.

Nonionic ethoxylated alcohol compounds are also known as softening agents and are preferred in the softening compositions of the invention. These compounds have the generic formula $$R_{22}-O(C_2H_4O)_xH \qquad (7)$$

where $R_{22}$ represents an alkyl of from 20 to 30 carbon atoms, and X is an integer of from 3 to 45.

The particularly preferred ethoxylated alcohol compounds of this class are the condensation products of reacting from 3 moles to 45 moles of ethylene oxide with one mole of eicosyl alcohol, heneicosyl alcohol, tricosyl alcohol, pentacosyl alcohol, or hexacosyl alcohol. Specific examples of the particularly preferred ethoxylated alcohols include the following reaction products of:
3 moles ethylene oxide + 1 mole of heneicosyl alcohol,
9 moles ethylene oxide + 1 mole eicosyl alcohol,
12 moles ethylene oxide + 1 mole hexacosyl alcohol,
15 moles of ethylene oxide + 1 mole tetracosyl alcohol,
20 moles of ethylene oxide + 1 mole pentacosyl alcohol, and
30 moles of ethylene oxide + 1 mole tricosyl alcohol.

Other preferred ethoxylated alcohols are the condensation products of from 3 moles to 45 moles of ethylene oxide with one mole of heptacosyl, octacosyl, nonacosyl, or triacontyl alcohols. Specific examples include the condensation products of the following:
5 moles of ethylene oxide + 1 mole of nonacosyl alcohol,
6 moles of ethylene oxide and 1 mole of heptacosyl alcohol,
9 moles of ethylene oxide + 1 mole of octacosyl alcohol,
20 moles of ethylene oxide + 1 mole of heptacosyl alcohol,
30 moles of ethylene oxide + 1 mole of triacontyl alcohol, and
40 moles of ethylene oxide + 1 mole of nonacosyl alcohol.

Also suitable for use as softening agents in the compositions herein are nonionic synthetic detergents as represented by the polyethylene oxide condensates of aliphatic alcohols containing from 8 to 20 carbon atoms and alkylphenols wherein the alkyl contains from 8 to 20 carbon atoms. Particularly preferred are the condensation products of 1 mole of tallow alcohol with 20 moles and with 30 moles of ethylene oxide, hereinafter designated $TAE_{20}$ and $TAE_{30}$ respectively.

Particularly preferred nonionic fabric softeners include the esterified cyclic dehydration products of sorbitol, i.e., sorbitan esters. The description and preparation of sorbitan esters is described in U.S. Pat. No. 4,022,938 assigned to The Procter and Gamble Company.

Sorbitan esters of lauric, myristic, palmitic, stearic and behenic acids are particularly useful. Mixed sorbitan esters, for example mixtures of the foregoing esters, and mixtures prepared by esterifying sorbitan with fatty acids, are also useful. Unsaturated $C_{10}$–$C_{18}$ sorbitan esters, e.g., sorbitan oleates, are also usually present in such mixtures. It is to be understood that all sorbitan esters, and mixtures thereof, which are essentially water-insoluble and which have fatty hydrocarbyl "tails," are useful fabric softeners in the context of the present invention.

Examples of tri- and tetra-sorbitan esters include sorbitan trilaurate, sorbitan trimyristate, sorbitan tripalmitate, sorbitan tristearate, sorbitan tribehenate, sorbitan tetralaurate, sorbitan tetramyristate, sorbitan tetrapalmitate, sorbitan tetrastearate, sorbitan tetrabehenate and mixtures thereof.

Another useful group of nonionic fabric softeners are the substantially water-insoluble compounds chemically classified as fatty alcohols. Mono-ols, di-ols and poly-ols having the requisite melting points and water-insolubility properties set forth above are useful herein. Such alcohol-type materials also include the mono- and di-fatty glycerides which contain at least one "free" OH group.

All manner of water-insoluble, high melting alcohols (including mono- and di-glycerides), can usefully be employed on fabric softeners, inasmuch as all such materials can be deposited onto fabric surfaces.

A preferred type of unesterified alcohol includes the higher melting members of the so-called fatty alcohol class. Although once limited to alcohols obtained from natural fats and oils, the term "fatty alcohols" has come to mean those alcohols which correspond to the alcohols obtainable from fats and oils, and all such alcohols can be made by synthetic processes. Fatty alcohols prepared by the mild oxidation of petroleum products can useful be employed. Examples of suitable fatty alcohols are those which contain from 10 to 22 carbon atoms, preferably 14 to 20 carbon atoms. These include dodecanol, tetradecanol, cetyl alcohols, octadecanol, eicosanol and tallow fatty alcohol. Tallow alcohol is preferred.

Another type of material which can be classified as an alcohol and which can be employed as a fabric softener is chosen from various esters of polyhydric alcohols. Such "ester-alcohol" materials which have a melting point within the range defined herein and which are substantially water-insoluble can be employed when they contain at least one free hydroxyl group, i.e., when they can be classified chemically as alcohols.

The alcoholic di-esters of glycerol include both the 1,3-di-glycerides and the 1,2-di-glycerides. In particular, di-glycerides containing two $C_8$–$C_{18}$ preferably $C_{10}$–$C_{18}$ alkyl groups in the molecule are useful fabric softeners.

Examples of ester-alcohols include:
glycerol-1,2-dilaurate; glycerol-1,3-dilaurate; glycerol-1,2-myristate; glycerol-1,3-dimyristate; glycerol-1, 2-dipalmitate; glycerol-1,3-dipalmitate; glycerol-1, 2-distearate and glycerol-1,3 distearate. Mixed glycerides available from mixed tallowalkyl fatty acids, i.e., 1,2-ditallowalkyl glycerol and 1,3-ditallowalkyl glycerol, are also useful.

Mono- and di-ether alcohols, especially the $C_{10}$–$C_{18}$ di-ether alcohols having at least one free —OH group, also fall within the definition of alcohols useful as fabric softeners. The ether-alcohols can be prepared by the classic Williamson ether synthesis. As with the ester-alcohols, the reaction conditions are chosen such that at least one free, unetherified —OH group remains in the molecule.

Ether-alcohols include glycerol-1,2-dilauryl ether; glycerol-1,3-distearyl ether; and butane tetra-ol-1,2,3-trioctanyl ether.

Of all the above types of nonionic fabric softeners, the most preferred are the $C_{14-18}$ alkyl sorbitan tri- and tetra-esters. In particular, such compounds as sorbitan tristearate, sorbitan tetrastearate, sorbitan tripalmitate, sorbitan tetrapalmitate, the tallowalkyl tri-ester of sorbitan and the tallowalkyl tetra-ester of sorbitan are highly preferred.

Also preferred as softening agents in the compositions herein are anionic ethoxylated alcohol sulfates and anionic sulfonates.

The preferred ethoxylated alcohol sulfates have the generic formula

$$R_{23}-O(C_2H_4O)_xSO_3-M+ \qquad (8)$$

where X is an integer of from 1 to 20, M is an alkali metal (e.g., Na, K, Li), ammonium or substituted ammonium cations, and where $R_{23}$ is an alkyl containing from 20 to 30 carbon atoms.

The particularly preferred anionic ethoxylated alcohol sulfate softening compounds are the sodium and potassium salts of the monoethanol, diethanol, or triethanol ammonium salts of the sulfated condensation product of from 1 to about 20 moles of ethylene oxide with one mole of eicosyl alcohol. Specific examples of these particularly preferred anionic softening compounds include the salts of the sulfated condensation products of the following:

1 mole of ethylene oxide + 1 mole of tetracosyl alcohol 3 mole of ethylene oxide + 1 mole of hexacosyl alcohol, 9 moles of ethylene oxide + 1 mole of tricosyl alcohol, 12 moles of ethylene oxide + 1 mole of eicosyl alcohol, 16 moles of ethylene oxide + 1 mole of pentacosyl alcohol, and 29 moles of ethylene oxide + 1 mole of heneicosyl alcohol.

Other preferred anionic ethoxylated sulfate compounds are the sodium or potassium salts or monoethanol, diethanol, or triethanol ammonium cations of the sulfated condensation products of from 1 to 20 moles of ethylene oxide with one mole of heptacosyl alcohol, octacosyl alcohol, nonacosyl alcohol, and triacontyl alcohol.

Anionic synthetic detergents as represented by alkyl sulfates of the formula

$$R_{24} - OSO_3^- M^+ \qquad (9)$$

wherein M is an alkali metal and $R_{24}$ is an alkyl of from 8 to 20 carbon atoms are also useful as softening agents.

The preferred anionic sulfates have the general formula

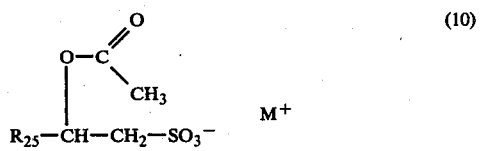

(10)

where M is an alkali metal or a substituted ammonium cation, and $R_{25}$ is an alkyl containing from 20 to 30 carbon atoms. The particularly preferred anionic sulfonates are those in which $R_{25}$ is an alkyl containing from 20 to 26 carbon atoms. Examples of the particularly preferred compounds include:

sodium or potassium 2-acetoxydocosylsulfonate,
ammonium 2-acetoxydocosylsulfonate,
diethanolammonium 2-acetoxydocosylsulfonate,
sodium or potassium 2-acetoxytricosylsulfonate,
sodium or potassium 2-acetoxytetracosylsulfonate,
sodium or potassium 2-acetoxypentacosylsulfonate,
sodium or potassium 2-acetoxyhexacosylsulfonate,
sodium or potassium 2-acetoxyheptacosylsulfonate and sodium or potassium 2-acetoxyoctacosylsulfonate Other preferred anionic sulfonates include sodium or potassium:
2-acetoxynonacosylsulfonate,
2-acetoxytriacontylsulfonate,
2-acetoxyheneitriacontylsulfonate and
2-acetoxydotriacontylsulfonate.

Other anionic sulfonates useful as softening agents herein are the synthetic detergents as represented by, among others, sodium or potassium alkylbenzenesulfonates and sodium alkylglycerylethersulfonates having the configuration of Formula 10 above, wherein $R_{25}$ is an alkylbenzene or alkylglycerylether with the alkyl containing from 10 to 20 carbon atoms.

Additionally, ampholytic synthetic detergents of the formula

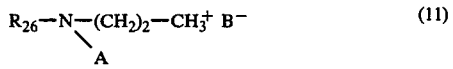
(11)

where $R_{26}$ is an alkyl of from 8 to 18 carbon atoms, A is $R_{26}$ or hydrogen, and B is a water-solubilizing group (particularly $SO_3$), can be used as softening agents.

Anionic soaps, i.e. the sodium salts of long-chain fatty acids, such as lauric, myristic, palmitic, stearic and arachidonic acids, can also be used as a softening agent in the compositions herein, and many such compounds are known in the art.

Smectite-type inorganic clays for use as fabric softeners are impalpable clays having particle sizes below 50 microns; preferably the clays have a particle size range of from 5 microns to 50 microns.

The clay minerals can be described as expandable, three-layer clays, i.e., alumino-silicates and magnesium silicates, having an ion exchange capacity of at least 50 meq/100g of clay. The term "expandable" as used to describe clays relates to the ability of the layered clay structure to be swollen, or expanded, on contact with water. The three-layer expandable clays are those materials classified geologically as smectites.

There are two distinct classes of smectite-type clays; in the first, aluminium oxide is present in the silicate crystal lattice; in the second class of smectites, magnesium oxide is present in the silicate crystal lattice. The general formulas of these smectites are $Al_2 (Si_2O_5)_2 (OH)_2$ and $Mg_3(Si_2O_5) (OH)_2$ for the aluminium oxide and magnesium oxide type clay, respectively. it is to be recognized that the range of the water of hydration in the above formulas can vary with the processing to which the clay has been subjected. This is immaterial to the use of the smectite clays in the present invention in that the expandable characteristics of the hydrated clays are dictated by the silicate lattice structure. Furthermore, atom substitution by iron and magnesium can occur within the crystal lattice of the smectites, while metal cations such as $Na^+$, $Ca^{++}$, as well as $H^+$, can be co-present in the water of hydration to provide electrical neutrality.

The three-layer, expandable alumino-silicates are further characterized by a dioctahedral crystal lattice, while the expandable three-layer magnesium silicates have a trioctahedral crystal lattice. These clays also have an ion exchange capacity of at least about 50 meq/100 g.

The smectite clays include, for example, montmorillonite, volchonskoite, nontronite, hectorite, saponite, sauconite and vermicutite.

While any of the smectite-type clays having a cation exchange capacity of at least about 50 meq/100 g. are useful herein, certain clays are preferred. For example, Gelwhite GP is an extremely white form of smectite clay and is therefore preferred when formulating white granular detergent compositions. Volclay BC, which is a smectite-type clay mineral containing at least 3% of iron (expressed as $Fe_2O_3$) in the crystal lattice, and which has a very high ion exchange cpacity, is one of the most efficient and effective clays for use in the compositions of the invention and is preferred from the standpoint of product performance.

Appropriate clay minerals for use herein can be selected by virtue of the fact that smectites exhibit a true 14 Å x-ray diffraction pattern. This characteristic pattern, taken in combination with exchange capacity measurements provides a basis for selecting particular smectite-type minerals for use in the compositions disclosed herein.

The fabric softeners disclosed above provide a comprehensive list from which a single fabric softener or an admixture of softeners can be chosen.

The amount of fabric softener employed in the fabric conditioner composition will depend on whether the composition is employed in the form of a solid or a liquid or whether impregnated into a solid substrate or carrier from which it can be transferred to fabric during a washing, rinsing or drying step as part of a laundry process.

In general, it can be stated that the fabric softener will form from 1 to 99.99%. For rinse added liquid fabric conditioning composition, the preferred amount of fabric softener is from 5 to 40% by weight. For dryer added impregnated substrate systems, the preferred amount of fabric softener is from 25 to 99% by weight.

Deodorant Perfume

The essential materials required for the formulation of deodorant perfumes that are operative according to the new principle are those that depress the partial vapour pressure of morpholine by at least 10% more than that required by Raoult's Law, as determined by the following test, which is designated "The Morpholine Test."

The Morpholine Test

In this test the capacity of a perfume material to depress the partial vapour pressure of morpholine more than that required by Raoult's Law is measured. Substances that undergo chemical reaction with morpholine are to be regarded as excluded from the test, even though they will generally depress the partial vapour pressure of morpholine by at least the defined amount, since not all such substances are operative according to the new principle. It is to be understood, however, that such substances can be included in the formulation of the deodorant perfume, provided that, when included, the composition has the ability to reduce odour intensity by at least 0.50 as herein defined.

The morpholine test is carried out in the following manner:

Into a sample bottle of capacity 20 ml is introduced morpholine (1g) the bottle fitted with a serum cap and then maintained at 30° C. for 30 minutes for equilibrium to be reached. The gas in the headspace of the bottle is analysed by piercing the serum cap with a capillary needle through which nitrogen at 30° C. is passed to increase the pressure in the bottle by a standard amount and then allowing the excess pressure to inject a sample from the headspace into gas chromatograph apparatus, which analyses it and provides a chromatographic trace curve with a peak due to morpholine, the area under which is proportional to the amount of morpholine in the sample.

The procedure is repeated under exactly the same conditions using instead of morpholine alone, morpholine (0.25g) and the perfume material to be tested (1g); and also using the perfume material (1g) without the morpholine to check whether it gives an interference with the morpholine peak (which is unusual).

The procedure is repeated until reproducible results are obtained. The areas under the morpholine peaks are measured and any necessary correction due to interference by the material is made.

A suitable apparatus for carrying out the above procedure is a Perkin-Elmer Automatic GB Multifract F40 for Head Space Analysis. Further details of this method are described by Kolb in "CZ-Chemie-Technik," Vol 1, No 2, 87–91 (1972) and by Jentzsch et al in "Z. Anal. Chem." 236, 96–118 (1968)

The measured areas representing the morpholine concentration are proportional to the partial vapour pressure of the morpholine in the bottle headspace. If A is the area under the morpholine peak when only morpholine is tested and A' is the area due to morpholine when a perfume material is present, the relative lowering of partial vapour pressure of morpholine by the perfume material is given by $1 - A'/A$.

According to Raoult's Law, if at a given temperature the partial vapour pressure of morpholine in equilibrium with air above liquid morpholine is p, the partial vapour pressure p' exerted by morpholine in a homogeneous liquid mixture of morpholine and perfume material at the same temperature is $p^M/(M+PC)$, where M and PC are the molar concentrations of morpholine and perfume material. Hence, according to Raoult's Law the relative lowering of morpholine partial vapour pressure $(p-p')/p$, is given by $1-M/(M+PC)$, which under the circumstances of the test is $87/(87+m/4)$, where m is the molecular weight of the perfume material.

The extent to which the behaviour of the mixture departs from Raoult's Law is given by the ratio $$\frac{1-A'/A}{87/(87+m/4)}$$

The above ratio, which will be referred to as the Raoult variance ratio, is calculated from the test results. Where a perfume material is a mixture of compounds, a calculated or experimentally determined average molecular weight is used for m. A perfume material that depresses the partial vapour pressure of morpholine by at least 10% more than that required by Raoult's Law is one in which the Raoult variance ratio is at least 1.1.

Deodorant perfumes can be incorporated in fabric conditioner compositions according to the invention, at a concentration of from about 0.01 to about 10%, preferably from 0.05 to 3% and most preferably from 0.1 to 1% by weight.

It is apparent that if less than 0.01% of a deodorant perfume is employed, then use of faric conditioner composition is unlikely to result in a significant reduction in odour intensity. If more than 10% of a deodorant perfume is employed, then the fabric conditioner composition might further reduce odour intensity beyond that observed at the 10% level, but use of a composition containing such a high level of perfume could result in the fabric being "over-perfumed" and therefore unacceptable for the wearer.

Fabric Conditioning Adjuncts

In addition to the fabric conditioning composition comprising conventional fabric softeners and deodorant perfume, there may be present certain fabric conditioning materials which in general do not act as fabric softeners. For purposes of the present invention, a fabric conditioning adjunct is any material which is not a fabric softener, as herein defined and which improves or modifies the chemical or physical characteristics of the fabric being treated therewith.

The choice of fabric conditioning adjunct that can optionally be incorporated in the composition will generally depend on the physical form of the composition and also on the point of addition to the fabric during the laundry cycle (ie soak, wash, rinse or dry). Examples of such fabric conditioning adjuncts include:

(1) Water-soluble detergent actives including any of the common anionic, nonionic, ampholytic and zwitterionic detergent actives well known in the detergency arts. Examples of detergent actives are as follows.

Water-soluble salts of the higher fatty acids, i.e., "soaps" are useful anionic detergent actives. This class of detergent actives includes ordinary alkali metal soaps such as the sodium, potassium, ammonium and alkanolammonium salts of higher fatty acids containing from about 8 to about 24 carbon atoms and preferably from about 10 to 20 carbon atoms. Soaps can be made by direct saponification of fats and oils or by the neutralization of free fatty acids. Particularly useful are the sodium and potassium salts of the mixtures of fatty acids derived from coconut oil and tallow, i.e., sodium or potassium tallow and coconut soaps.

Another class of anionic detergent actives includes water-soluble salts, particularly the alkali metal, ammonium and alkanolammonium salts, of organic sulfuric reaction products having in their molecular structure an alkyl group containing from about 8 to about 22 carbon atoms and a sulfonic acid or sulfuric acid ester groups. (Incuded in the term "alkyl" is the alkyl portion of acyl groups.) Examples of this group of synthetic detergent actives which can be used are the sodium and potassium alkyl sulfates, especially those obtained by sulfating the high alcohols ($C_8$–$C_{18}$ carbon atoms) produced by reducing the glycerides of tallow or coconut oil; and sodium and potassium alkyl benzene sulfonates, in which the alkyl group contains from about 9 to about 15 carbon atoms in straight chain or branched chain configuration.

Other anionic detergent actives include the sodium alkyl glyceryl ether sulfonates, especially those esters or higher alcohols derived from tallow and coconut oil; sodium coconut oil fatty acid monoglyceride sulfonates and sulfates; and sodium or potassium salts of alkyl phenol ethylene oxide ether sulfate containing about 1 to about 10 units of ethylene oxide per molecule and wherein the alkyl groups contain about 8 to about 12 carbon atoms.

Other useful anionic detergent actives include the water-soluble salts of esters of α-sulfonated fatty acids containing from about 6 to 20 carbon atoms in the ester group; water-soluble salts of 2-acyloxy-alkane-1-sulfonic acids containing from about 2 to 9 carbon atoms in the acyl group and from about 9 to about 23 carbon atoms in the alkane moiety; alkyl ether sulfates containing from about 10 to 20 carbon atoms in the alkyl group and from about 1 to 30 moles of ethylene oxide; water-soluble salts of olefin sulfonates containing from about 12 to 24 carbon atoms; and β-alkyloxy alkane sulfonates containing from about 1 to 3 carbon atoms in the alkyl group and from about 8 to 20 carbon atoms in the alkane moiety.

Preferred water-soluble anionic organic detergent actives include linear alkyl benzene sulfonates containing from about 11 to 14 carbon atoms in the alkyl group; the tallow range ($C_{12-20}$) alkyl sulfates; the coconut range alkyl glyceryl sulfonates; and alkyl ether sulfates wherein the alkyl moiety contains from about 14 to 18 carbon atoms and wherein the average degree of ethoxylation varies between 1 and 6.

Specific preferred anionic detergent actives for use in the fabric conditioning compositions include; sodium linear $C_{10}$–$C_{12}$ alkyl benzene sulfonate; triethanolamine $C_{10}$–$C_{12}$ alkyl benzene sulfonate; sodium tallow alkylsulfate; and sodium coconut alkyl glyceryl ethers sulfonate; and the sodium salt of a sulfated condensation product of tallow alcohol with from about 3 to about 10 moles of ethylene oxide.

It is to be understood that any of the foregoing anionic detergent actives when employed can be used separately or as mixtures.

Nonionic detergent actives include the water-soluble ethoxylates of $C_{10}$–$C_{20}$ aliphatic alcohols and $C_6$–$C_{12}$ alkyl phenols. Many nonionic detergent actives are especially suitable for use as suds controlling agents in combination with detergent actives of the type disclosed hereinbefore.

Semi-polar detergent actives include water-soluble amine oxides containing one alkyl moiety of from about 10 to 28 carbon atoms and 2 moieties selected from alkyl groups and hydroxyalkyl groups containing from 1 to about 3 carbon atoms; water-soluble phosphine oxides containing one alkyl moiety of about 10 to 28 carbon atoms and 2 moieties selected from alkyl groups and hydroxyalkyl groups containing from about 1 to 3 carbon atoms; and water-soluble sulfoxides containing one alkyl moiety of from about 10 to 28 carbon atoms and a moiety selected from alkyl and hydroxyalkyl moieties of from 1 to 3 carbon atoms.

Ampholytic detergent actives include derivatives of aliphatic or heterocyclic secondary and tertiary amines in which the aliphatic moiety can be straight chain or branched and wherein one of the aliphatic substituents contains from about 8 to 18 carbon atoms and at least one aliphatic substituent contains an anionic water-solubilizing group.

Zwitterionic detergent actives include derivatives of aliphatic quaternary ammonium, phosphonium and sulfonium compounds in which the aliphatic moieties can be straight or branched chain, and wherein one of aliphatic substituents contains from about 8 to 18 carbon atoms and one contains an anionic water-solubilizing group.

When the fabric conditioning compositions are used as presoaking or wash additive compositions in conjunction with other commercially available laundry detergent products, the detergent active component generally comprises from about 0% to 7% by weight of the compositions, preferably from about 2% to 6% by weight. When the fabric conditioning compositions are to be used as the sole detergent product during the laundering process, the detergent active component generally comprises from about 5% to 25%, preferably from about 10 to 20% by weight of the composition.

(2) Detergency builders including inorganic and organic water-soluble builder salts, as well as various water-insoluble and so-called "seeded" builders.

Inorganic detergency builders include, for example, water-soluble salts of phosphates, pyrophosphates, orthophosphates, polyphosphates, phosphonates, carbonates, bicarbonates, borates and silicates. Specific examples of inorganic phosphate builders include sodium and potassium tripolyphosphates, phosphates, and hexametaphosphates. The polyphosphonates specifically include, for example, the sodium and potassium salts of ethylene diphosphonic acid, the sodium and potassium salts of ethane 1-hydroxy-1, 1-diphosphic acid, and the sodium and potassium salts of ethane-1,1,2-triphosphonic acid. Sodium tripolyphosphate is an especially preferred, water-soluble inorganic builder.

Non-phosphorous containing sequestrants can also be selected for use as detergency builders. Specific examples of non-phosphorus, inorganic builder ingredients include water-soluble inorganic carbonate, bicarbonate, borate and silicate salts. The alkali metal, e.g., sodium and potassium, carbonates, bicarbonates, borates (Borax) and silicates are particularly useful.

Water-soluble, non-phosphorous organic builders are also useful. For example, the alkali metal, ammonium and substituted ammonium polyacetates, carboxylates polycarboxylates, succinates, and polyhydroxysulfanates are useful builders in the present compositions and processes. Specific examples of the polyacetate and polycarboxylate builder salts include, sodium, potassium, lithium, ammonium and substituted ammonium salts of ethylene diamine tetraacetic acid, nitrilotriacetic acid, oxydisuccinic acid, mellitic acid, benzene polycarboxylic acids, and citric acid.

Highly preferred non-phosphorous builders (both organic and inorganic) include sodium carbonate, sodium bicarbonate, sodium silicate, sodium citrate, sodium oxydisuccinate, sodium mellitate, sodium nitrilotriacetate, and sodium ethylenediaminetetraacetate, and mixtures thereof.

Another type of detergency builder comprises a water-soluble material capable of forming a water-insoluble reaction product with water hardness cations in combination with a crystallization seed which is capable of providing growth sites for said reaction product.

Specific examples of materials capable of forming the water-insoluble reaction product include the water-soluble salts of carbonates, bicarbonates, sequicarbonates, silicates, aluminates and oxalates. The alkali metal, especially sodium, salts of the foregoing materials are preferred for convenience and economy.

Another type of builder useful herein includes various substantially water-insoluble materials which are capable of reducing the hardness content of laundering liquors, e.g., by ion-exchange processes.

The complex aluminosilicates, i.e., zeolite-type materials, are useful presoaking/washing adjuvants in that these materials soften water, i.e., remove $Ca^{++}$ hardness. Both the naturally occurring and synthetic "zeolites", especially zeolite A and hydrated zeolite A materials, are useful for this builder/softener purpose.

When the fabric conditioning compositions are used as presoaking or wash additive compositions in conjunction with other commercially available laundry detergent products, the detergency builder component generally comprises from about 30% to 90%, preferably from about 50% to 75% by weight of the composition. When the fabric conditioning compositions are to be used as the sole detergent product during the laundering process, the detergency builder component generally comprises from about 25% to 75%, preferably from about 30% to 50% by weight of the composition.

(3) Optical brighteners, ie fluorescent brightening agents such as substituted disulphonated diaminostilbene and triazole compounds.

(4) Essential oils and fragrances which are not deodorant perfumes.

(5) Antistatic agents, which in many cases are compounds of the same general structures discussed above with respect to fabric softening compounds. Specific antistatic agents which may be mentioned by way of example are ethoxylated compounds such as ethoxylated amines, ethoxylated quaternary ammonium compounds, ethoxylated aliphatic alcohols or alkyl phenols, ethoxylated carbohydrates such as sorbitol ethoxylates, ethoxylated aliphatic mono- or di-carboxylic acids, amides or esters thereof, or polyethylene glycols. The antistatic properties of the preferred quaternary ammonium compounds as well as other fabric softening agents may be enhanced in particular by combining these materials with ethoxylated amides such as tallow ethanolamides, or with ethoxylated aliphatic alcohols.

(6) Germicides, such as the halogenated salicylanilides, eg trichlorocarbanilide, tribromosalicylanilide, trichlorohydroxydiphenyl ether, hexachlorophene, neomycin sulphate, benzalkonium quaternary compounds, and the like.

(7) Bodying agents, such as carboxymethylcellulose, hydroxyethylcellulose, starch, polyvinyl acetate and the like. Polyvinyl acetate is also effective to improve ease of ironing and may be employed for that purpose.

(8) Soil release agents, such as polyacrylic acid, polymethacrylic acid, polyvinyl alcohol, poly (acrylic acid-ethyl acrylate), alkyl celluloses, alkylhydroxyalkyl celluloses, hydroxyalkyl celluloses, fluorocarbons and copolymers of ethylene glycol with terephthalic acid which are useful for treating polyester fabrics for this purpose.

(9) Ironing aids, for example silicones such as dimethyl silicone.

(10) Bleaches commonly employed in pre-soak, laundry additive and detergent compositions. Such bleaches can include, for example, the various organic peroxyacids such as peradipic acid, perphthalic acid, diperphthalic acid, disperazelaic acid and the like. Inorganic bleaches, i.e. persalts including such materials as sodium perborate, sodium perborate tetra-hydrate, urea peroxide, and the like, can be employed in the compositions. Bleaches can be used at a level of from about 1% to 45% by weight of the composition.

An especially preferred bleaching agent is sodium perborate tetrahydrate, at an effective concentration of from about 10% to about 30% by weight of the total composition.

(11) Detergency enzymes well known in the art for their ability to degrade and aid in the removal of various soils and stains. Detergency enzymes are commonly used at concentrations of from about 0.1% to about 1.0% by weight of such compositions. Typical enzymes include th various proteases, lipases, amylases, and mixtures thereof, which are designed to remove a variety of soils and stains from fabrics.

In addition to the above-described adjuncts the compositions can optionally contain a wide variety of other conventional detergency adjuncts. Representative materials of this type include, for example, the various anti-caking agents, filler materials, elasticity improving agents, flame proofing agents, pleating agents, anti-spotting agents, water repelling agents, crease proofing agents, acid repelling agents, antishrinking agents, heat proofing agents and colouring material. These detergency adjuncts are commonly used as minor components (e.g., 0.1% to 5% wt.) in compositions of the present type.

Such fabric conditioning adjuncts must, however, be selected with care in order to insure their compatibility with the fabric softener and deodorant perfume. Thus, the fabric conditioning adjunct utilized should be inert to chemical reaction with the fabric softener.

The fabric conditioning adjunct selected should also contain no substances which would tend to physically interact with the fabric softener or deodorant perfume, in a manner which would interfere with their respective softening and deodorising properties.

In addition to being chemically inert it is essential that the compounds of the fabric conditioning adjuncts used have relatively high boiling points. Components which have boiling points below particular values are generally too volatile for use. Accordingly, components of the fabric conditioning adjuncts utilized in the present invention must have boiling points in excess of about 100° C., preferably about 200° C. For the purposes of the present invention, those fabric conditioning adjuncts components which have no reported boiling point, i.e. those which decompose before boiling, but which are chemically stable at 100° C. (or 200° C.), are considered to have boiling points in excess of 100° C. (or 200° C.). The total amount of fabric conditioning adjuncts that can be incorporated into the fabric conditioning composition according to the invention will normally form the balance of the composition after accounting for the deodorant perfume and fabric conditioner. The fabric conditioning adjuncts will accordingly form from 0 to 98.99% by weight of the composition.

Preparation and Use of Solid Fabric Conditioning Compositions

The fabric conditioning compositions can be solid in form, for example as particulate or granular solids or prills which are intended for addition to the presoak, wash, rinse or drying sequence of a laundry process.

The solid compositions can be prepared simply by admixing conventional detergent granules containing detergent actives and/or builders with the above-described fabric softener and deodorant perfume. The first step of the fabric conditioning method of the present invention can be carried out simply by adding the above-described solid compositions to the warm (less than 45° C.) presoaking or washing liquor during the laundering operation. Such compositions can be dissolved/dispersed to the extent of from about 0.05% to 1.0%, preferably from about 0.07% to 0.2%, by weight of the presoaking, washing or rinse liquor, or they can be added to the damp laundry load in a tumble drier at the rate of from 0.02 to 10g, preferably from 1 to 2g per 2kg laundry load expressed on a dry weight basis.

Preparation and Use of Liquid Fabric Conditioning Compositions

The fabric conditioning compositions can be liquid in form, for example as flowable thickened liquids, optionally containing dissolved or dispersed solids, which are intended for addition to the presoak, wash or rinse sequence of a laundry process. The liquid conditioning composition can also be in a form suitable for spraying onto a damp laundry load prior to drying.

Liquid fabric conditioning compositions can be prepared simply by mixing the composition ingredients in any desirable order. Some agitation is generally necessary to insure proper dispersion of the insoluble ingredients, proper suspension of solids and proper dissolution of the soluble materials.

Such liquid fabric conditioning compositions can be used to carry out the first step of the fabric conditioning method. The liquid compositions can be added to the presoak, wash or rinse water at the rate of from 0.01 to 0.5%, preferably from 0.02 to 0.3% by weight of the water.

Preparation and Use of Impregnated Substrate Fabric Conditioning Articles

The fabric conditioning compositions, can as has been stated above, be employed by simply adding a measured amount of the composition into the soak, wash or rinse water or into the dryer. However, in a preferred embodiment, the fabric conditioning compositions are provided as an article of manufacture in combination with a dispensing means which effectively releases the softening compositions in a tumble dryer. Such dispensing means can be designed for single usage or for multiple uses. They can also be employed by adding them to the soak, wash or rinse water.

One such article comprises a sponge material releasably enclosing enough of the conditioning composition to effectively impart fabric softness and deodorancy during several drying cycles. This multi-use article can be made by filling a hollow sponge with about 20g of the composition. In use, the composition melts and leaches out through the pores of the sponge to soften fabrics. Such a filled sponge can be used to treat several loads of fabrics in conventional dryers, and has the advantage that it can remain in the dryer after use and is not likely to be misplaced or lost.

Another article comprises a cloth or paper bag releasably enclosing the composition and sealed with a hardened plug of the mixture. The action and heat of the dryer opens the bag and releases the composition to perform its softening and delivery of deodorant perfume function.

Still another article comprises an aerosol cannister containing the above-described compositions under pressure. The composition can be dispensed from this aerosol article into the dryer drum.

A highly preferred article comprises the compositions containing the softener and deodorant perfume releasably affixed to a sheet of paper or woven or non-woven cloth substrate. When such an article is placed in an automatic laundry dryer, the heat and tumbling action of the dryer removes the composition from the substrate and deposits it on the fabrics.

The sheet conformation has several advantages. For example, effective amounts of the compositions for use in conventional dryers can be easily sorbed onto and into the sheet substrate by a simple dipping or padding process. Thus, the user need not measure the amount of the composition necessary to obtain fabric softness. Additionally, the flat configuration of the sheet provides a large surface area which results in efficient release of the softener materials onto fabrics by the tumbling action of the dryer.

The water-insoluble paper, or woven or non-woven substrates used in the articles can have a dense, or more preferably, open or porous structure. Examples of suitable materials which can be used as substrates herein include paper, woven cloth, and non-woven cloth. The term "cloth" herein means a woven or non-woven substrate for the articles of manufacture, as distinguished from the term "fabric" which encompasses the clothing fabrics being dried in an automatic dryer.

It is known that most substances are able to absorb a liquid substance to some degree; however, the term "absorbent", as used herein, is intended to mean a non-woven textile substrate with an absorbent capacity (i.e., a parameter representing a substrate's ability to take up and retain a liquid) from 4 to 12, preferably 5 to 7, times its weight of water.

If the substrate is a foamed plastics material, the absorbent capacity is preferably in the range from 15 to 22, but some special foams, for example reticulated foams, can have an absorbent capacity in the range from 4 to 12.

Determination of absorbent capacity values is made by using the capacity testing procedures described in U.S. Federal Specifications (UU-T-595b, modified as follows:

1. tap water is used instead of distilled water;
2. the specimen is immersed for 30 seconds instead of 3 minutes;
3. draining time is 15 seconds instead of 1 minute; and
4. the specimen is immediately weighed on a torsion balance having a pan with turned-up edges. Absorbent capacity values are then calculated in accordance with the formula given in said Specification. Based on this test, one-ply, dense bleached paper (e.g., Kraft or bond having a basis weight of about 32 pounds per 3,000 square feet) has an absorbent capacity of 3.5 to 4; commercially available household one-ply toweling paper has a value of 5 to 6; and commercially available two-ply household toweling paper has a value of 7 to about 9.5.

Suitable materials which can be used as a substrate in the invention herein include, among others, sponges, paper, and woven and non-woven cloth, all having the necessary absorbency requirements defined above. The preferred substrates of the softening compositions herein are cellulosic, particularly multi-ply paper and non-woven cloth. More specifically, a preferred paper substrate comprises a compressible, laminated, calendered, multi-ply, absorbent paper structure. Preferably, the paper structure has 2 or 3 plies and a total basis weight of from 20 to 140g per square metre and absorbent capacity values within the range of 7 to 10. Each ply of the preferred paper structure has a basis weight of about 10 to 50g per square metre, and the paper structure can consist of plies having the same or different basis weights. Each ply is preferably made from a creped, or otherwise extensible, paper with a creped percentage of about 15% to 40% and a machine direction (MD) tensile and cross-machine (CD) tensile of from about 15 to 250g per square cm of paper width. The two outer plies of a 3-ply paper structure of each ply of a 2-ply structure are embossed with identical repeating patterns consisting of about 2 to 30 discrete protuberances per square cm, raised to a height of from about 2.5mm to 10mm above the surface of the unembossed paper sheet. From about 10% to 60% of the paper sheet surface is raised. The distal ends (i.e. the ends away from the unembossed paper sheet surface) of the protuberances on each ply are mated and adhesively joined together, thereby providing a preferred paper structure exhibiting a compressive modulus of from about 30 to 120cm — g per cm$^2$ and Handle-O-Meter (HOM) MD and CD values of from about 10 to 130.

The preferred non-woven cloth substrates can generally be defined as adhesively bonded fibrous or filamentous products having a web or carded fiber structure (where the fiber strength is suitable to allow carding), or comprising fibrous mats in which the fibers or filaments are distributed haphazardly or in random array (i.e. an array of fibers in a carded web wherein partial orientation of the fibers is frequently present, as well as a completely haphazard distributional orientation), or substantially aligned. The fibers or filaments can be natural (e.g. wool, silk, jute, hemp, cotton, linen, sisal, or ramie) or synthetic (e.g. rayon, cellulose ester, polyvinyl derivatives, polyolefins, polyamides, or polyesters).

The preferred absorbent properties are particularly easy to obtain with non-woven cloths and are provided merely by building up the thickness of the cloth i.e., by superimposing a plurality of carded webs or mats to a thickness adequate to obtain the necessary absorbent properties, or by allowing a sufficient thickness of the fibers to deposit on the screen. Any diameter or denier of the fiber (generally up to about 10 denier) can be used, inasmuch as it is the free space between each fiber that makes the thickness of the cloth directly related to the absorbent capacity of the cloth, and which, further, makes the non-woven cloth especially suitable for impregnation with a composition by means of intersectional or capillary action. Thus, any thickness necessary to obtain the required absorbent capacity can be used.

When the substrate for the composition is a non-woven cloth made from fibers deposited haphazardly or in random array on the screen, the articles exhibit excellent strength in all directions and are not prone to tear or separate when used in the automatic clothes dryer.

Preferably, the non-woven cloth is water-laid or air-laid and is made from cellulosic fibers, particularly from regenerated cellulose or rayon. Such non-woven cloth can be lubricated with any standard textile lubricant. Preferably, the fibers are from 5mm to 50mm in length and are from 1.5 to 5 denier. Preferably, the fibers are at lest partially oriented haphazardly, particularly substantially haphazardly, and are adhesively bonded together with a hydrophobic or substantially hydrophobic binder-resin, particularly with a nonionic self-crosslinking acrylic polymer or polymers. Preferably, the cloth comprises about 70% fiber and 30% binder-resin polymer by weight and has a basis weight of from about 18 to 45g per meter squared.

EXAMPLES OF THE INVENTION

This invention is illustrated by the following examples.

EXAMPLE 1

This example illustrates the treatment of shirts with a liquid fabric conditioning composition which is added during the rinse cycle of a laundry process.

Forty polyester cotton shirts were washed, line dried and then rewashed according to the standard procedure described hereinbefore for liquid fabric conditioning treatment during the rinse cycle of a laundry process. Twenty of the shirts were treated as test shirts and the remaining twenty as control shirts.

The formulation of the fabric conditioning composition employed was as follows:

| | | |
|---|---|---|
| ARQUAD 2HT (Di-(hardened tallow) dimethyl ammonium chloride) | | 6 |
| Deodorant perfume (Formulation A4) | | 0.2 |
| Formaldehyde | | 0.015 |
| Sodium chloride | | 0.04 |
| Colouring matter | | 0.0005 |
| Deionised water | to | 100 |

The formulation of the deodorant perfume was as follows:

| Deodorant Perfume Formulation A4 | PARTS |
|---|---|
| Bergamot AB 430 | 8.00 |
| p-t-Butylcyclohexyl acetate | 4.30 |
| Citronella oil | 6.00 |
| Diethyl phthalate | 8.25 |
| Ethyl vanillin | 0.20 |
| iso-Eugenol | 5.00 |
| Green Herbal AB 502 | 15.00 |
| 2-n-Heptylcyclopentanone | 0.50 |
| Indole | 1.50 |
| Inonyl formate | 5.00 |
| LRG 201 | 1.25 |
| α-iso-Methyl ionone | 5.00 |
| β-Napthol methylether | 7.50 |
| Nonanediol-1:3-diacetate | 4.00 |
| Patchouli oil | 7.00 |
| Phenylethyl phenyl acetate | 5.00 |
| Rosenta AB 380 | 6.00 |
| Sandalone | 4.00 |
| Tetrahydro muguol | 6.00 |
| γ-Undecalactone | 0.50 |
| | 100.00 |

The deodorant perfume treated and control shirts were assessed according to the standard test procedure as described hereinbefore.

The results of the modified Whitehouse and Carter test were as follows:

| | Control Composition | Test Composition |
|---|---|---|
| Average Scores | 2.62 | 1.54 |

The reduction in odour intensity of the test composition was the difference between these two scores which was 1.08. This was well in excess of 0.50 which defines the lower limit of reduction of odour intensity (odour reduction value) of compositions of the invention.

EXAMPLE 2

This example illustrates the treatment of shirts with a liquid fabric conditioning composition which is added during the rinse cycle of a laundry process.

Forty polyester cotton shirts were washed, line dried and then rewashed according to the standard procedure described hereinbefore for liquid fabric conditioning treatment during the rinse cycle of a laundry process. Half of the shirts were treated as test shirts and the remainder as control shirts.

The formulation of the fabric conditioning composition employed was as follows:

|  | % W/W |
|---|---|
| ARQUAD 2HT | 3 |
| AMMONYX 4080 (Dialkyl ($C_{16}$–$C_{18}$) imidazoline methosulphate) | 3 |
| Deodorant perfume (Formulation B6) | 0.2 |
| Formaldehyde | 0.0075 |
| Sodium chloride | 0.02 |
| Colouring matter | 0.0025 |
| Deionised water to | 100 |

The formulation of the deodorant perfume was as follows:

| Deodorant Perfume Formulation B6 | PARTS |
|---|---|
| Benzyl Propionate | 4.0 |
| Bergamot Oil | 15.0 |
| o-t-Butylcyclohexyl acetate | 2.0 |
| p-t-Butyl-α-methyl hydrocinnamic aldehyde | 15.0 |
| Clove leaf oil | 10.0 |
| Diethyl Phthalate | 9.25 |
| Dimethyl benzyl carbinyl acetate | 5.0 |
| Inony acetate | 10.0 |
| Iso-Butyl Benzoate | 5.0 |
| LRG-201 | 1.25 |
| 3a-Methyl-dodecahydro-6,6,9a,trimethylnaphtho-2(2,1-b)-furan | 0.5 |
| Neroli Oil | 3.0 |
| Petitgrain Oil | 10.0 |
| Phenyl ethyl alcohol | 10.0 |
|  | 100 |

The test and control shirts were assessed according to the standard test procedure as described hereinbefore.

The results of the modified Whitehouse and Carter test were as follows:

|  | Control Composition | Test Composition |
|---|---|---|
| Average Scores | 2.42 | 1.36 |

The reduction in odour intensity of the test composition was the difference between these two scores, which was 1.06. This was well in excess of 0.50 which defines the lower limit of reduction of odour intensity (odour reduction value) of compositions of the invention.

EXAMPLE 3

This example illustrates the treatment of shirts with a substrate impregnated fabric conditioning composition which is added to a damp laundry load immediately prior to tumble drying.

Forty polyester cotton shirts were washed, line dried and rewashed and tumble dried according to the procedure described hereinbefore for substrate impregnated fabric conditioning composition treatment during the tumble drying sequence of a laundry process. Half of the shirts were treated as test shirts and the remainder as control shirts.

The formulation of the fabric conditioning composition employed to impregnate the standard substrate tissue (of the type described hereinbefore with reference to the standard and test procedure) was as follows:

|  | % W/W |
|---|---|
| di-(hardened tallow) dimethyl ammonium chloride | 75 |
| condensation product of a secondary linear ($C_{11}$–$C_{15}$) alcohol with 12 moles of ethylene oxide | 25 |

The formulation of the deodorant perfume (B6) was that described in Example 2.

The test and control shirts were assessed according to the standard test procedure as described herein before.

The results of the modified Whitehouse and Carter test were as follows:

|  | Control Composition | Test Composition |
|---|---|---|
| Average Scores | 2.48 | 1.74 |

The reduction in odour intensity of the test composition was the difference between these two scores, which was 0.74. This was well in excess of 0.50 which defines the lower limit of reduction of odour intensity (odour reduction value) of compositions of the invention.

EXAMPLES 4 TO 7

Results similar to that described in Examples 1 to 3 can be obtained by employing any of the following deodorant perfume formulations:

| Deodorant Perfume Formulation Cl | Parts |
|---|---|
| Amber AB 358 | 3.0 |
| iso-Amyl salicylate | 5.0 |
| Benzyl salicylate | 4.0 |
| Bergamot AB 430 | 15.0 |
| o-t-Butylcyclohexyl acetate | 0.5 |
| Cedar atlas oil | 5.0 |
| Citronellol | 7.0 |
| Citronella oil | 16.1 |
| Citronellyloxyacetaldehyde | 0.5 |
| Geranium base 76 | 4.0 |
| 1,3,4,6,7,8-Hexahydro-4,6,6,7,8,8-hexamethyl cyclopenta-γ-2-benzopyran | 10.0 |
| Hexyl aldone | 0.7 |
| Jasmin AB 284 | 12.0 |
| LRG 201 | 5.0 |
| Nonanolide-1:4 | 0.2 |
| Opoponax resinoid | 1.7 |
| Orange oil sweet | 8.0 |
| 10-Undecen-1-al | 0.30 |
| Vetyvert oil | 2.0 |
|  | 100.00 |

| Deodorant Perfume Formulation D2 | PARTS |
|---|---|
| 6-Acetyl-1,1,3,4,4,6-hexamethyl-tetrahydro naphthalate | 3.00 |
| Bergamot base 37 | 20.00 |
| Carvacrol | 3.50 |
| Citronellyl acetate | 5.00 |
| Dipropylene glycol | 4.75 |
| Geranyl nitrile | 1.50 |
| Indole | 1.00 |
| Lemongrass oil | 3.00 |
| Lime AB 402 | 10.00 |
| Lavandin oil | 4.00 |
| 1-Menthol | 8.00 |
| 3a-Methyl-dodecahydro-6,6,9a-trimethyl naphtho-2(2,-b)-furan | 0.25 |
| β-Methyl naphthyl ketone | 5.00 |
| β-Napthol methyl ether | 9.00 |
| Neroli base 78 | 6.00 |
| Pomeransol AB 314 | 6.00 |
| Petitgrain oil (terpeneless) | 4.00 |
| Orange oil sweet | 5.00 |
| Thyme oil red | 1.00 |
|  | 100.00 |

| Deodorant Perfume Formulation E3 | PARTS |
|---|---|
| p-t-Amylcyclohexanone | 5.00 |
| Benzoin Siam resinoid | 5.00 |
| Bergamot AB 430 | 15.00 |
| Coumarin | 4.00 |
| Diethyl phthalate | 4.35 |
| Geranium oil | 5.00 |
| Hercolyn D | 12.25 |
| 1,3,4,6,7,8-Hexahydro-4,6,6,7,8,8-hexamethyl cyclopenta-γ-2-benzopyran | 3.00 |
| Lavandin oil | 10.00 |
| α-iso-Methyl ionone | 12.00 |
| Mousse de chene yugo | 1.25 |
| Musk ambrette | 3.00 |
| Pimento leaf oil | 10.00 |
| Rosenta AB 380 | 10.00 |
| Rose-D-oxide | 0.15 |
|  | 100.00 |

| Deodorant Perfume Formulation F5 | PARTS |
|---|---|
| 6-Acetyl-1,1,3:4,4,6-Hexamethyl tetrahydro naphthalate | 2.5 |
| p-t-Amylcylohexanone | 0.06 |
| Benzyl Salicylate | 15.0 |
| Bergamot AB 430 | 15.0 |
| Cinnamic Alcohol | 5.0 |
| Diethyl Phthalate | 8.04 |
| Dimethyl benzyl carbinyl acetate | 2.5 |
| Dimyrcetol | 16.0 |
| Dipropylene glycol | 14.25 |
| Geraniol | 5.0 |
| Isobutyl phenyl acetate | 5.0 |
| 3a-,methyl-dodecahydro-6,6,9a-trimethyl-naphtho-2(2,1-b) furan | 0.75 |
| Methyl Salicylate | 0.5 |
| Mousse de Chene Yougo | 6.0 |
| Nonanolide-1:4 | 0.2 |
| Pelargene | 4.0 |
| Trichloromethyl phenyl carbinyl acetate | 0.2 |
|  | 100.00 |

APPENDIX

The following glossary provides further information, including the suppliers' names, which will aid identification of some of the aforementioned perfume components and ingredients.

All materials which are classified by a name and number are obtainable from Proprietary Perfumes Limited.

| | |
|---|---|
| Dimyrcetol | — Dimyrcetol (IFF) |
| Hercolyn D | — Tetrahydro abietate + dihydro abietate (HP) |
| LRG 201 | — Oakmoss speciality (RB) |
| Pelargene | — Pelargene (PPL) |
| Rose-D-Oxide | — Rose oxide synthetic (PPL) |
| Sandalone | — Sandalone (PPL) |

Perfume Houses
HP — Hercules Powder Co.
IFF — International Flavour & Fragrances Inc.
RB — Roure Bertrand
PPL — Proprietary Perfumes Limited

What is claimed is:

1. A fabric conditioning composition comprising an effective amount of from 1 to 99.99% by weight of a fabric softener and a deodorising amount of from 0.01 to 10% by weight of a deodorant perfume, and from 0 to 98.99% by weight of fabric conditioning adjuncts, the fabric conditioning composition having an odour reduction value within the range of from 0.50 to 3.5 as measured by the modified Whitehouse and Carter test.

2. A composition according to claim 1, wherein the fabric softener is a cationic fabric softener selected from the group consisting of quaternary ammonium salts, quaternary imidazolinium salts, alkylated diamines, acylated diamines, their salts and mixtures thereof.

3. A composition according to claim 1, wherein the fabric softener is a nonionic fabric softener selected from the group consisting of tertiary phosphine oxides, tertiary amine oxides, ethoxylated alcohols, alkyl phenols, and mixtures thereof.

4. A composition according to claim 1, wherein the fabric softener is an anionic fabric softener selected from the group consisting of fatty acid soaps, ethoxylated alcohol sulphates, sodium alkyl sulphates, alkyl sulphonates, sodium alkyl benzene sulphonates, sodium or potassium alkyl glycol ether sulphonates, and mixtures thereof.

5. A composition according to claim 1, wherein the fabric softener is a zwitterionic quaternary ammonium compound.

6. A composition according to claim 1, in which the fabric softener is an ampholytic tertiary ammonium compound.

7. A composition according to claim 1, having an odour reduction value of at least 0.60.

8. A composition according to claim 1, having an odour reduction value of at least 0.80.

9. A composition according to claim 1, having an odour reduction value of at least 1.00.

10. A composition according to claim 1, having an odour reduction value of at least 1.20.

11. A process for preparing a deodorant fabric conditioning composition according to claim 1, which process comprises mixing from 0.01 to 10% by weight of a deodorant perfume, and from 1 to 99.99% by weight of a fabric softener and from 0 to 98.99% by weight of fabric conditioning adjuncts to provide a fabric conditioner composition having an odour reduction value within the range of from 0.50 to 3.5 as measured by the modified Whitehouse and Carter test.

12. A method for suppressing human body malodour which comprises contacting the skin with a fabric treated with an effective amount of a fabric conditioning composition according to claim 1.

* * * * *